United States Patent
Huang et al.

(10) Patent No.: US 8,778,048 B2
(45) Date of Patent: Jul. 15, 2014

(54) BIOCHEMICAL HUMIC ACID PRODUCT PREPARED FROM KITCHEN WASTE AND THE METHOD OF PREPARING THE SAME

(75) Inventors: Qian Huang, Beijing (CN); Yu Haiyan, Beijing (CN)

(73) Assignee: Beijing Goldenway Bio-Tech Co., Ltd., Beijing (CN)

( * ) Notice: Subject to any disclaimer, the term of this patent is extended or adjusted under 35 U.S.C. 154(b) by 274 days.

(21) Appl. No.: 13/205,929

(22) Filed: Aug. 9, 2011

(65) Prior Publication Data

US 2012/0047974 A1 Mar. 1, 2012

(30) Foreign Application Priority Data

Aug. 31, 2010 (CN) .......................... 2010 1 0269356

(51) Int. Cl.
*C05F 11/08* (2006.01)
*A62D 3/02* (2007.01)

(52) U.S. Cl.
USPC ..................... 71/8; 71/9; 71/10; 435/262.5

(58) Field of Classification Search
USPC .................................... 435/262.5; 71/8, 9, 10
See application file for complete search history.

(56) References Cited

U.S. PATENT DOCUMENTS

| | | | | |
|---|---|---|---|---|
| 3,674,649 A | * | 7/1972 | Formisano et al. | 435/142 |
| 4,459,149 A | * | 7/1984 | Moran et al. | 71/24 |
| 6,664,100 B2 | * | 12/2003 | Reverso | 435/262.5 |
| 2009/0241623 A1 | * | 10/2009 | Matano et al. | 71/9 |

FOREIGN PATENT DOCUMENTS

CN 200610083429.7 5/2006

OTHER PUBLICATIONS

Liqian, H. Definition of Biotechnology Fulvic Acid (BFA). 1999.
Shuji, X, et al. Significant Effects of Humic Acid Fertilizer on Improving Barren Soil. 1989.
Li Li, et al. General Situation of Research on the Synergistic Effect of Humic Acid on Phosphorus Fertilizer. 1998.
Jun, L., Lifeeng, L., Qing, Z. Experiences at home and abroad and research progress on turning kitchen waste into feedstuff. 2009.
Qing, Z., et al. Analysis of Present Situation of Kitchen Waste Used as Animal Feed and Countermeasures in China. 2010.
Kexing, L. et al. Bio-humic Acid: The Important Foreland of Exploitating New Resources and Functions of Modern Fertilizer. 2008.
Shuiying, Y. Studies and Manufacture of Biochemically-Humic Acid Fertilizer. 1999.
Westendorf, Mi., Dong, Z.C., and Schoknecht, P.A. Recycled Cafeteria food waste as a feed for swine; nutrient content digestibility, growth, and meat quality. Journal of Animal Science 1998, 76: 2976-2983.

* cited by examiner

*Primary Examiner* — Wayne Langel
(74) *Attorney, Agent, or Firm* — McDonald Hopkins LLC

(57) ABSTRACT

The present invention discloses a new resource processing method of kitchen waste, in particular, provides a method of preparing biochemical humic acid from kitchen waste and biochemical humic acid product prepared therefrom. The kitchen waste treated by technical solution of the present invention has a high conversion rate of organic matter, reaching over 90%. Meanwhile, the biochemical humic acid product prepared by the invention is nutritious, the amount of the total humic acid, free humic acid and water soluble humic acid in the product reach up to 38-42%, 35-40% and 14-16%, respectively; it contains not only the major elements such as nitrogen, phosphorus and potassium, but also the trace elements such as zinc, iron and manganese as well as other active substances. Thus the product is suitable for fertilizer in agricultural production.

9 Claims, No Drawings

BIOCHEMICAL HUMIC ACID PRODUCT PREPARED FROM KITCHEN WASTE AND THE METHOD OF PREPARING THE SAME

CROSS-REFERENCE TO RELATED APPLICATION

This application claims priority to Chinese Application No. 201010269356.7 filed on Aug. 31, 2010.

TECHNICAL FIELD

The present invention relates to a resource processing method of kitchen waste (mainly containing organic ingredients and water), especially relates to a method of preparing biochemical humic acid from kitchen waste and biochemical humic acid product prepared by this method.

BACKGROUND

Natural humic acid, which is formed from the plant and animal remains after long-term and complicated biochemical reaction, mainly exists in soil and lean coal such as peat coal, weathered coal and brown coal. Natural humic acid belongs to un-renewable natural resources, and its alkaline extract, called coal humic acid or mineral humic acid, is the current major humic acid product which has realized industrialization and has been used in industry and agriculture. However, biochemical humic acid (BHA) is a product rich in humic acid, which is produced from the organic waste as raw material by special biochemical process. The available organic wastes from industry, agriculture and daily life are mainly crop straw, food processing waste, excrement of livestock and poultry, residue of sugar industry, black liquid from paper industry, waste liquid of alcohol and gourmet powder, garden waste etc. Thus, BHA is an "artificial humic acid" and a new source of humic acid. Since the raw material of BHA is the waste instead of natural resource, developing BHA can effectively solve the problem of depending on un-renewable natural resources. Research (He Liqian, 1999) shows that, BHA not only has general characteristics and properties of the humic acid, but also has characteristics different from ordinary humic acid: 1) having low extent of condensation, low carbon content, and small molecular weight, being easy to be absorbed and utilized by organisms; 2) containing more functional groups, having stronger physiological activity than ordinary humic acid; 3) having light color, and better water solubility, being soluble in acidic or alkaline solution; 4) having high flocculation limit and big buffer capacity.

In agricultural production, the humic acid fertilizer possesses the following significant efficacy: increasing production and improving quality. The humic acid and trace elements in humic acid fertilizer form a complex compound or chelate compound which is easily dissolved and easy to be absorbed by crops, which is helpful for root system and leaf surface to absorb trace elements. The functional groups of humic acid such as carboxyl, phenolic hydroxyl group, which have strong ion exchange and adsorption ability, can reduce the loss of ammonium nitrogen to increase the utilization rate of nitrogen fertilizer; inhibit soil to fix the water-soluble phosphorus, change quick-acting phosphorus into slow-acting phosphorus and enhance the root system to absorb phosphorus; absorb and store potassium ion so as to make the potassium fertilizer degrade slowly, increase the release amount of the potassium, and thus increase the amount of quick-acting potassium. A variety of active functional groups in the humic acid molecular can enhance physiological metabolism, as well as growth and development of plants. Thus, the humic acid fertilizer can effectively increase utilization rate of the nutrients and stimulate the growth of crops, thus increasing yield and quality of crops.

The humic acid fertilizer also possesses the following significant efficacy: improving the resistance of crops. The humic acid fertilizer can decrease opening extent of plant leaf stomata and reduce leaf transpiration, thus decreasing water consumption of plant, improving the internal water condition in plant and enhancing its anti-drought ability. The humic acid fertilizer also can inhibit fungi, strengthen disease resistance of crops, avoid rot disease, root rot disease etc., and alleviate the damage from diseases and insect pest.

The humic acid fertilizer also possess the following significant efficacy: improving soil and reducing pollution. The humic acid fertilizer can enhance the formation of soil granular structure, reduce soil bulk density, increase the substitution amount of positive ion, and adjust soil acidity and alkalinity, so as to increase the soil's ability of water retention, fertilizer retention, heat preservation and ventilation.

The physicochemical properties of humic acid endows it the following advantages to serve as a fertilizer:

1. Improvement of Low Yield Soil: two thirds of the area of cultivated land in China is low-middle yield soil. Research (Xing Shuji, 1989) indicates that, applying large quantity of humic acid fertilizer throughout China can lead to a certain improvement in the arable soil or rhizosphere soil. There is a large area of red soil distributed in south China, the characteristics of such red soil are "acidic, barren, hard and dried", as well as lacking organic matter and nutrients, and having bad soil structure. The saline-alkali soils in China are mainly distributed in northwest China, north China, northeast China and the coastal areas, including saline soil and alkali soil. The major harms of the saline-alkali soils are: high soil salt content, too high concentration of the harmful ions; too high soil alkalinity; bad soil structure; inhibition of the growth and development of crops. Applying large quantity of the humic acid fertilizer for a long time can enhance the formation of soil aggregate and adjust the soil condition of "water, fertilizer, air and heat"; and can also inhibit the increase of salinity, reduce salt content of the topsoil, and change the pH values of saline-alkali soils through "salt-separating" and "salt-absorbing" effects, thus greatly increasing the survival rate of crops.

2. Increase of Effect and Slow Release of Chemical Fertilizer: at present in China, the utilization rate of nitrogen fertilizer, phosphorus fertilizer and potassium fertilizer accounts for about 20% to 30%, 10% to 20% and 50% to 70% respectively. How to improve the utilization rate of chemical fertilizer has become a very important research topic in the world. The humic acid fertilizer, which is produced through adding nitrogen, phosphorus, potassium and trace elements to the raw materials of peat coal, brown coal and weathered coal, can improve the utilization rate of chemical fertilizer in different degrees; this result has been verified by a large number of research reports from China and abroad (Li Li et al., 1998). For example, the typical nitrogen fertilizer such as urea and ammonium bicarbonate generally have high volatility and low utilization rate. However, their absorption can be improved and the utilization rate can be increased by 20% to 40% after mixing the nitrogen fertilizers with humic acid to form a humic acid fertilizer. Addition of nitro humic acid to urea can form a complex of humic acid and urea, make the decomposition of urea slow, prolong the fertilizer efficiency, and reduce the loss, so that the production-increasing effect of urea can be relatively increased by 30%, and the fertilizer efficiency can be increased by over 15%. The determination results of the utilization rate of nitrogen fertilizer indicates that, after adding humic acid, the utilization rate is increased from 30.1% to 34.1%, and the nitrogen uptake is increased by 10%.

3. Modulation of Growth and Development of Crops: the efficient biological active substances contained in the humic acid fertilizer can enhance physiological metabolism, growth and development of crops, and this characteristics is not possessed by ordinary fertilizer. The ways including seed soaking, root soaking, spraying, irrigating and being as base-fertilizer with a certain concentration of humic acid fertilizer have significant effects of stimulation on various crops. Applying humic acid fertilizer improves seed germination, and the germination rate is increased by 10% to 30%; root dipping or root soaking with humic acid fertilizer has become an agriculture technical measure to improve survival rate in sticking or transplanting. Applying humic acid fertilizer makes the crops grow very well, and improves the yield and quality of the crops. Applying humic acid fertilizer can also effectively increase the anti-drought and anti-frigidity abilities of crops, and prevent underground plant diseases, insect pests and pathogenic bacteria.

Kitchen waste refers to leftover bits and pieces and leftovers derived from hotels, restaurants, dining-halls etc., and it comprises processed food products and their residues, such as foodstuff (rice and flour), fruits and vegetables, plant and animal fats, meats, aquatic product, eggs, meat bones, and fish bone, etc. (Li Jun et al., 2009). The major chemical ingredients of kitchen waste are starch, protein, fat, cellulose, inorganic salt, which has high content of moisture, generally reaching up to 60% to 80%. There are mainly three types of kitchen waste in China: 1. domestic kitchen waste, which is classified into household kitchen waste by the China Ministry of Housing and Urban-Rural Development in 2009; 2. kitchen waste from dining-halls, restaurants, hotels, and staff dining-halls of government agencies, enterprises and public institutions, which is also an important source of kitchen waste; 3. kitchen waste from dining-halls of colleges and universities. According to a statistics from the Department of Environmental Science and Engineering in Tsinghua University, over 60 million tons of kitchen waste is generated in urban areas of China every year. The kitchen waste reaches up to 1200 tons in Beijing every day (Zhang Qing et al., 2010). The kitchen waste in China has a big total amount, and contains much fat, moisture, salt and other complex ingredients; if not treated properly, it is likely to cause food security problems such as "illegal cooking oil", "swill-feeding swine", thus resulting in wasting resources and influencing the ecological environment.

Generally speaking, the technology and policy on kitchen waste treatment in China are experiencing an exploring stage, and the management system and corresponding policy on kitchen waste treatment are being improved. At present the general ways of treating kitchen waste includes landfilling, burning, feed-processing technology and aerobic fermentation composting. Landfilling may cause the waste of land, while it will produce a great quantity of malodorous gas and permeated liquid, thus leading to secondary pollution to environment; burning treatment consumes much energy and produces cancer-causing substance dioxin; feed-processing technology is one of the major ways of kitchen waste treatment. In addition, illegally transporting the kitchen waste to farm for feeding swine or refining the "illegal cooking oil" causes secondary pollution to environment and potential safety harzard. The quality of fertilizers produced by anaerobic fermentation composting is poor; meanwhile, high-quality composting ways cost too much, and thus are difficult to disseminate. Since the current ways of treating kitchen waste lead to some problems in different extent, it is desired to develop a new process and new technology to increase the level of resource processing of kitchen waste.

Since 1980s, the experiment and research work regarding large-scale harmless utilization of kitchen waste has begun in some countries including Germany, France, UK, Cuba, Netherlands, US, Japan and South Korea. Achievements in the methods of collecting and treating kitchen waste and the products of kitchen waste processing have been obtained; also large-scale factories of treating kitchen waste are built in medium and large-sized cities; the treatment of kitchen waste has realized the specialization and its management has been legalized (Li Jun, 2009). At present, the major ways of treating kitchen waste out of China are also focusing on composting, landfilling, feed-processing technology and power generation and heat supply with biogenic gas. In US, the treatment ways mainly include recycling, composting and being feed; in US, the treatment way of composting is used in the Middle-West area, mainly in prisons and schools where the kitchen waste is centrally collected. Currently, vermicomposting and in-vessel composting are generally applied. The traditional treatment way in Japan is composting, which can transforms the food waste into organic fertilizers and soil conditioners. In recent years, feed-processing technology is the major way of treating kitchen waste in some of East Asian countries such as South Korea and Japan which have large population with relatively little land.

At present, the method of preparing BHA in China and abroad is performed by inoculating a plurality of special microbial bacteria strains in plant medium, namely, agricultural organic waste such as crop straw, saw dust and bagasse, fermenting by chemical or microbial fermentation technology and isolating to obtain BHA (Liu Kexing et al., 2008; Ye Shuiying, 1999). There is no report in China and abroad on producing biochemical humic acid from kitchen waste as culture medium.

DETAILED DESCRIPTION

The object of the present invention is to provide a new resource processing method of kitchen waste, especially relates to a method of preparing biochemical humic acid from kitchen waste and a biochemical humic acid product prepared by this method.

As the raw material for preparing BHA, kitchen waste has its unique advantages: 1) huge resource: the amount of diet consumption of 1.3 billion of population in China is very big. Counting on the basis that one person produces 0.1 kg kitchen waste per day, there will be 50 million tons of kitchen waste in a year. Such rich kitchen waste provides sufficient materials for preparing BHA. 2) High nutrition with rich trace elements: the research result of Westendorf, et al. (1998) indicates that, the kitchen waste of cafeteria comprises 22.4% of dry substance, 21.4% of crude protein, 14.1% of crude fiber, 27.2% of crude fat and 3.2% of ashes. Furthermore, the kitchen waste also contains rich mineral elements including calcium, magnesium, iron and potassium. This shows that there are high nutrient ingredients and rich trace elements in the kitchen waste. 3) Turning waste into treasure, realizing the recycle of the resources and solving the problems of wasting resources and polluting the environment caused by burying or burning the kitchen waste as household rubbish.

Aiming at the blank space of the existing research work on biochemical humic acid and the characteristics of kitchen waste, the inventor of the present invention ferments the kitchen waste with high temperature BGB compound bacteria after repeated experiments and prepares a biochemical humic acid product which comprises high content of humic acid, complete nutrient elements and rich trace elements, as well as conforming to the trend of recycling resource in industrial scale. The BGB compound bacteria involved in the present invention was disclosed in Chinese Patent Application No. 200610083429.7, filed in May 31, 2006, entitled "A resource processing method of kitchen waste with compound bacteria", and the compound bacteria comprise the following bacteria: *Bacillus subtilis, Bacillus circulans, Bacillus sphaericus, Bacillus stearothermophilus, Saccharomycete* and *Lactobacillus* etc. Each microbial strain can be picked from the strain cryopreserved by conventional methods, streak-inoculated in solid plate medium, and cultured under suitable conditions, when the colony grows out, the colony is inoculated into liquid medium to conduct shaking culture, and then conduct amplification culture as needed; after culturing in liquid medium, the above cultured strains can be mixed together to form a liquid fermenting agent in a ratio of (1-1.2):(0.8-1.1):(1.2-1.5):(2.2-3):(1.2-1.5):(0.8-1.2), based on the viable bacteria count of *Bacillus subtilis, Bacillus circulans, Bacillus sphaericus, Bacillus stearothermophilus, Saccharomycete* and *Lactobacillus*, and then stored at 4° C. for subsequent use; the strains also can be stored separately, mixed together for instant use; the liquid culture also can be freeze-dried into solid bacteria powder to give a solid fermenting agent. The applicant discovers that it (referred to as BGB high temperature compound bacteria, sold by Beijing Goldenway Bio-tech (BGB) Co., Ltd.) can produce many enzymes such as proteinase, lipase, amylase and endochitinase, and it can degrade the macro-molecular proteins and fats in organic substance into small molecular peptide and oligosaccharide; furthermore, the outstanding characteristic of the BGB compound bacteria lies in that it can normally ferment at high temperature (e.g., at 80° C.). The entire contents of Chinese Patent Application No. 200610083429.7 (Publication number: CN1850965A), are incorporated herein by reference.

A biochemical humic acid product prepared from kitchen waste, wherein the method of preparing the product comprises the following steps:

1) pretreating and sieving: sieving the collected kitchen waste without treatment to remove inorganic matters such as plastics, chopsticks, paper napkins, toothpicks and bottle caps, etc.;

2) culturing: amplifying the BGB high temperature compound bacteria by culture to obtain its compound bacteria culture;

3) mixing: well mixing the BGB high temperature compound bacteria culture, the sieved kitchen waste and water-adjusting substance, and adjusting moisture content of the mixture to 50-60%;

4) fermenting: fermenting at 60-80° C. for 8-10h. The water-adjusting substance in the step 3) is an agricultural organic waste including crop straws, saw dusts and bagasses which can adjust the moisture content of the whole mixed material to 50-60%.

BGB high temperature compound bacteria culture is added to the kitchen waste in the step 3) at the dosage of 0.25-0.30 g culture per 1 kg waste, and the number of viable bacteria per gram of the compound bacteria culture is $1.5 \times 10^8$-$2.0 \times 10^8$.

The method of preparing the product further comprises the following step after the step 4): drying the fermented material to make its moisture content no more than 10% and obtain the biochemical humic acid product.

After testing, the technical index of the biochemical humic acid product is listed as follows:

TABLE 1

| Test items | Technical index |
| --- | --- |
| Total humic acid ($HA_t$), d % | 38-42 |
| Free humic acid ($HA_f$), d % | 35-40 |
| Water-soluble humic acid (HAs), d % | 14-16 |
| Organic matter, d % | 85-90 |
| Moisture, d % | 3-5 |
| Total nitrogen content, d % | 1.6-1.9 |
| Potassium oxide ($K_2O$), d % | 0.6-0.8 |

In a specific embodiment according to the present invention, the process of preparing biochemical humic acid from kitchen waste according to the present invention comprises the following steps:

(1) sieving and mixing the raw material: the collected kitchen waste is sieved to remove inorganic matters, and fed into a conventional equipment (e.g., biochemical treatment machine) after weighing, in which agricultural organic waste (i.e. the water-adjusting substance, for example, adding 80 kg of peanut hull, wheat straw or rice hull into 120 kg of kitchen waste) is added to adjust the moisture content of the whole mixed materials to 50-60%, and make it become a growing environment suitable for rapidly activating the microbial strains. Then the high temperature compound bacteria culture is added to the kitchen waste at the dosage of 0.25-0.30 g culture per 1 kg waste, and the number of viable bacteria per gram of the compound bacteria culture is $1.5 \times 10^8$-$2.0 \times 10^8$.

(2) fermenting: the biochemical treatment machine is started, and the materials are mixed for 10 min, then the heating device, circulating wind-supply blower and air-exhaust ventilator are switched on, the materials are heated to 80° C. and kept at this temperature for 8 h. During this period, the circulating wind-supply blower constantly blows fresh air to the fermenting pool of the biochemical treatment machine while the treatment machine stirs the material constantly. Thus the microbial strains can get sufficient oxygen, and a condition suitable for the rapid proliferation and growth of BGB high temperature compound bacteria can be formed. The strains in the fermenting pool of the biochemical treatment machine proliferate to a large number, degrade the organic matters and transform them into small molecular bacteria proteins and metabolic oligosaccharides thereof. Additionally, heating the material to 80° C. is helpful to evaporate the moisture from the material slowly, and the evaporated steam is sucked by the air-exhaust ventilator. The high temperature during the fermentation of the material can kill harmful bacteria, and is helpful for the microbial strains to deodorize and converting salts.

(3) post-treating: the above treated material is further dried to make its moisture content no more than 10%, sieved and weighed as original powder of biochemical humic acid.

The above technical solution has advantages as follows:

1. Kitchen waste is a new resource for producing biochemical humic acid. The technical solution of the present invention changes the non-renewable coal humic acid into renewable biochemical humic acid, and thus makes great contribution to sustainable development of the humic acid industry and resolution of energy shortage. It is also a major development strategy and trend in the future.

At present, some ways of resource utilization of kitchen waste such as landfilling, burning and composting have the shortcomings of occupying the land, wasting resource and causing secondary environment pollution in different extent. Rather, preparing biochemical humic acid from kitchen waste can utilize over 99% of the resource and will not cause any pollution to the environment.

2. The present invention fills a technology gap in China on preparing biochemical humic acid from kitchen waste, providing a new method, technology and technical strategy for recycling of kitchen waste.

3. The preparation method of the present invention takes only 8-10 h, while 14 to 21 d is required for fermenting the kitchen waste in the conventional technology. The present invention can save time and reduce the energy consumption and production cost, thus making it possible for industrial operation to form industrial scale.

4. After treating the kitchen waste according to the technical solution of the present invention, the conversion rate of its organic matters is over 90%. Meanwhile, the biochemical humic acid product prepared from this method contains rich nutrients; the amount of the total humic acid, free humic acid and water soluble humic acid are 38-42%, 35-40% and 14-16% respectively; it contains not only major elements including nitrogen, phosphorus and potassium but also trace elements including zinc, iron and manganese and a plurality of active substances. The biochemical humic acid product is particularly suitable to be used as fertilizer in agricultural production.

EXAMPLES

Examples are described below to further illustrate the specific embodiments of the present invention. The following examples are used to explaining the invention, and the scope of the invention should not be limited by the examples.

Example 1

The biochemical humic acid according to the present invention is prepared by the following method:
1) pretreating and sieving: sieving the kitchen waste to remove inorganic matters;
2) culturing: amplifying by culture the BGB high temperature compound bacteria through conventional methods to obtain its compound bacteria culture;
3) mixing and fermenting: well mixing the BGB high temperature compound bacteria culture, the sieved kitchen waste and agricultural organic waste (water-adjusting substance) according to said mixing ratio, and then fermenting to obtain the biochemical humic acid product; wherein
kitchen waste: 120 kg;
peanut hull (water-adjusting substance): 80 kg;
BGB compound bacteria fermenting agent ($1.5 \times 10^8$ cfu/g): 30 g;
fermentation time: 8 h; fermentation temperature: 80° C.

Example 2

The preparation method is the same as Example 1, and the ratio of the raw materials are shown as follows:
kitchen waste: 120 kg;
water-adjusting substances: wheat straw 40 kg, peanut hull 40 kg, wherein the moisture content is adjusted to 55%;
BGB compound bacteria fermenting agent ($2.0 \times 10^8$ cfu/g): 30 g;
fermentation time: 10 h;
fermentation temperature: 60° C.

Example 3

The preparation method is the same as Example 1, and the ratio of the raw materials are shown as follows:
kitchen waste: 120 kg;
water-adjusting substances: rice hull 40 kg, peanut hull 40 kg, wherein the moisture content is adjusted to 60%;
BGB compound bacteria fermenting agent ($2.0 \times 10^8$ cfu/g): 30 g;
fermentation time: 8 h;
fermentation temperature: 80° C.

After testing, the technical index of the biochemical humic acid product from the above examples is listed as follows:

TABLE 2

| Technical index | Example 1 | Example 2 | Example 3 |
|---|---|---|---|
| Total humic acid ($HA_t$), d % | 41.29 | 39.63 | 40.68 |
| Free humic acid ($HA_f$), d % | 37.79 | 36.25 | 38.56 |
| Water-soluble humic acid (HAs), d % | 15.65 | 15.02 | 16.20 |
| Organic matter, d % | 85 | 87 | 89 |
| Moisture, d % | 3.07 | 3.97 | 4.18 |
| Total nitrogen content, d % | 1.86 | 1.77 | 1.65 |
| Potassium oxide ($K_2O$), d % | 0.79 | 0.65 | 0.73 |

The test standard of total humic acid and free humic acid is implemented as per Chinese GB/P11957-2001, and the test standard of water-soluble humic acid is implemented as per Chinese HG/P3278-87.

It can be seen from the above examples, after treating the kitchen waste according to the technical solution of the present invention, the conversion rate of its organic matters reaches over 90%. Meanwhile, the biochemical humic acid product prepared from this method contains rich nutrients; it contains not only major elements including nitrogen, phosphorus and potassium but also trace elements including zinc, iron and manganese and a plurality of active substances. The biochemical humic acid product is particularly suitable to be used as fertilizer in agricultural production.

Multiple-batch kitchen waste from 20 hotels in Beijing was treated according to the method of the present invention, and the results are substantially similar to those in the above examples.

Unless otherwise indicated, the percent sign "%" as used herein, means weight percent The above examples are merely the preferred embodiments of the present invention. It should be understood that, a person skilled in the art can make alterations or modifications of the present invention without departing from the spirit and essence thereof, and those alterations or modifications should fall in the scope of the invention.

What is claimed is:
1. A biochemical humic acid product, wherein the biochemical humic acid product comprises:
   38-42 wt % of total humic acid;
   35-40 wt % of free humic acid; and
   14-16 wt % of water-soluble humic acid; and
wherein the method of preparing the biochemical humic acid product comprises the following steps:
   1) sieving collected kitchen waste without treatment to remove inorganic matters;
   2) culturing a BGB high temperature compound bacteria, wherein the BGB high temperature compound bacteria includes *bacillus subtilis, bacillus circulans, bacillus sphaericus, bacillus stearothermophilus, saccharomycete*, and *lactobacillus*;

3) mixing the BGB high temperature compound bacteria culture, the sieved kitchen waste and water-adjusting substance, and adjusting moisture content of the mixture to 50-60%; and 4) fermenting at 60-80° C. for 8-10 h.

2. The biochemical humic acid product according to claim 1, wherein the biochemical humic acid product comprises 85-90 wt % of organic matter.

3. The biochemical humic acid product according to claim 1, wherein the biochemical humic acid product comprises:
   3-5 wt % of moisture;
   1.6-1.9 wt % of total nitrogen; and
   0.6-0.8 wt % of potassium oxide.

4. The biochemical humic acid product according to claim 1, wherein the water-adjusting substance is an agricultural organic waste which adjusts the moisture content of the whole mixed material to 50-60%.

5. The biochemical humic acid product according to claim 1 wherein BGB high temperature compound bacteria culture is added to the kitchen waste at a dosage of 0.25-0.30 g culture per 1 kg waste, and the number of viable bacteria per gram of the compound bacteria culture is $1.5 \times 10^8$-$2.0 \times 10^8$.

6. The biochemical humic acid product according to claim 1 wherein the method of preparing the product further comprises the following step of drying the fermented material to make its moisture content no more than 10% to obtain the biochemical humic acid product.

7. A method of preparing a biochemical humic acid product having 38-42 wt % of total humic acid, 35-40 wt % of free humic acid, and 14-16 wt % of water-soluble humic acid from kitchen waste, wherein the method comprises the following steps:

1) sieving the collected kitchen waste without treatment to remove inorganic matters;

2) culturing a BGB high temperature compound bacteria wherein the BGB high temperature compound bacteria includes *bacillus subtilis, bacillus circulans, bacillus sphaericus, bacillus stearothermophilus, saccharomycete*, and *lactobacillus;*

3) mixing the BGB high temperature compound bacteria culture, the sieved kitchen waste and water-adjusting substance, and adjusting moisture content of the mixture to 50-60%;

4) fermenting at 60-80° C. for 8-10 h so as to form said humic acid product.

8. The method according to claim 7, wherein the water-adjusting substance is an agricultural organic waste which adjusts the moisture content of the whole mixed material to 50-60%.

9. The method according to claim 7 wherein BGB high temperature compound bacteria culture is added to the kitchen waste at the dosage of 0.25-0.30 g culture per 1 kg waste, and the number of viable bacteria per gram of the compound bacteria culture is $1.5 \times 10^8$-$2.0 \times 10^8$.

* * * * *

UNITED STATES PATENT AND TRADEMARK OFFICE
CERTIFICATE OF CORRECTION

PATENT NO. : 8,778,048 B2  
APPLICATION NO. : 13/205929  
DATED : July 15, 2014  
INVENTOR(S) : Huang Qian and Yu Haiyan Page 1 of 1

It is certified that error appears in the above-identified patent and that said Letters Patent is hereby corrected as shown below:

Title page item (75), delete "Qian Huang" and insert --Huang Qian--

Signed and Sealed this  
Twenty-first Day of July, 2015

Michelle K. Lee  
*Director of the United States Patent and Trademark Office*